(12) United States Patent
Sanchez et al.

(10) Patent No.: US 12,728,043 B2
(45) Date of Patent: Sep. 8, 2026

(54) MEDICAL ARTICLE FOR FIXATION OF A WOUND DRESSING

(71) Applicant: PAUL HARTMANN AG, Heidenheim (DE)

(72) Inventors: Marc Sanchez, Barcelona (ES); Fernando Gonzalez Gómez-Arevalillo, Barcelona (ES); Marina Ciupke, Konigsbronn-Zang (ES); Axel Eckstein, Heidenheim (DE)

(73) Assignee: PAUL HARTMANN AG, Heidenheim (DE)

( * ) Notice: Subject to any disclaimer, the term of this patent is extended or adjusted under 35 U.S.C. 154(b) by 18 days.

(21) Appl. No.: 18/724,479

(22) PCT Filed: Jan. 23, 2023

(86) PCT No.: PCT/EP2023/051524
§ 371 (c)(1),
(2) Date: Jun. 26, 2024

(87) PCT Pub. No.: WO2023/144077
PCT Pub. Date: Aug. 3, 2023

(65) Prior Publication Data

US 2025/0090381 A1 Mar. 20, 2025

(30) Foreign Application Priority Data

Jan. 27, 2022 (EP) .................................... 22382060

(51) Int. Cl.
*A61F 13/02* (2024.01)

(52) U.S. Cl.
CPC ...... *A61F 13/0283* (2013.01); *A61F 13/0269* (2013.01)

(58) Field of Classification Search
CPC .. A61F 13/02; A61F 13/0259; A61F 13/0269; A61F 13/0276; A61F 13/0283;
(Continued)

(56) References Cited

U.S. PATENT DOCUMENTS 9,827,206 B2 * 11/2017 Guillermin ............. B29C 43/24
11,090,406 B1 * 8/2021 Cros .................. A61F 13/0253
(Continued)

FOREIGN PATENT DOCUMENTS

GB 2460149 A * 11/2009 ............. B32B 38/04
WO 2016/025266 A1 2/2016
(Continued)

OTHER PUBLICATIONS

PMC, Occurrence, toxicity and remediation of polyethylene terephthalate plastics, Jan. 13, 2022.*

*Primary Examiner* — Alireza Nia
*Assistant Examiner* — Andrew Jun-Wai Mok
(74) *Attorney, Agent, or Firm* — LEYDIG, VOIT & MAYER, LTD.

(57) ABSTRACT

The present invention relates to a medical article for fixation of a wound dressing as well as its use and manufacturing method. The medical article comprises a non-woven backing layer. A plastic film layer is attached to the bottom side of the non-woven backing layer. An adhesive silicone gel layer is then in turn attached to the bottom side of the plastic film layer. Preferably, the medical article is provided in the form of a roll. The medical article according to the present invention may provide an easy to apply, secure, skin-friendly, painless and gentle fixation of a primary dressing such as a compress on the body of a patient.

22 Claims, 3 Drawing Sheets

Figure 1:
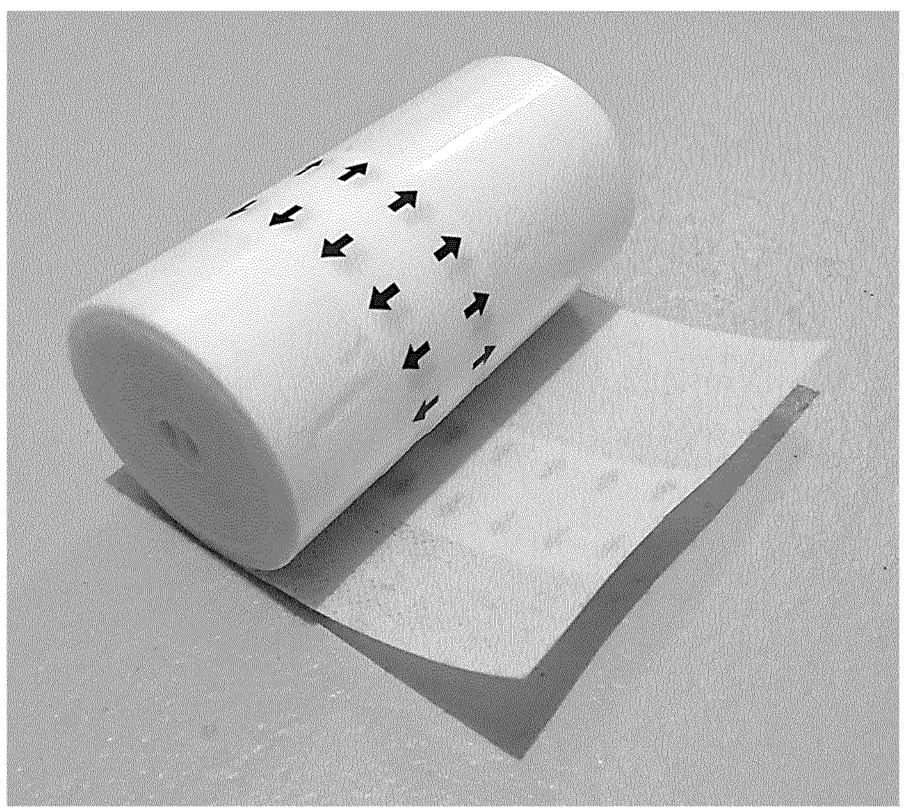

(58) Field of Classification Search
CPC ...... A61F 13/0289; A61L 15/00; A61L 15/42; A61L 15/44
See application file for complete search history.

(56) References Cited

U.S. PATENT DOCUMENTS

| | | | | |
|---|---|---|---|---|
| 2007/0270555 | A1 | 11/2007 | Jung et al. | |
| 2012/0253255 | A1* | 10/2012 | Tsuruta | A61F 13/0259 602/54 |
| 2013/0006203 | A1* | 1/2013 | Iwao | A61F 13/02 604/307 |
| 2017/0065459 | A1* | 3/2017 | Ragg | A61F 13/023 |
| 2020/0188183 | A1* | 6/2020 | Hamerslagh | A61F 13/0206 |

FOREIGN PATENT DOCUMENTS

| | | | | |
|---|---|---|---|---|
| WO | WO-2020188438 | A1 * | 9/2020 | C09J 7/50 |
| WO | WO-2021249890 | A1 * | 12/2021 | B32B 27/32 |

* cited by examiner

MEDICAL ARTICLE FOR FIXATION OF A WOUND DRESSING

The present invention relates to a medical article for fixation of a wound dressing. Moreover, the present invention relates to a use and a manufacturing method of the aforementioned medical article.

Medical articles for fixation of wound dressings are known in the prior art. They may essentially consist of a backing material, for example a flat non-woven layer, which is coated on one side with an adhesive. The adhesive may be covered by a releasable film layer to prevent contamination of the adhesive during storage and simplify the application of the medical article. Usually, adhesives having a high adhesive strength, such as for instance synthetic rubber-based adhesives, are employed to coat the backing material. Such adhesives may provide a secure fixation of the wound dressing on the body of the patient.

In wound treatment, such medical articles are typically used as follows. In a first step, the wound is covered with a wound dressing. The wound dressing itself comprises no adhesive component and is sometimes designated as primary dressing. A traditional primary wound dressing material is a gauze compress. In a second step, the medical article is attached with its adhesive layer to the primary dressing and the skin surrounding the wound to fix the primary dressing on the body of the patient. The medical article may be sized to completely cover the primary dressing, such that the medical article forms the outermost layer of the final wound dressing. In this context, the medical article is sometimes designated as secondary dressing. The secondary dressing contrary to the primary dressing is not intended for direct wound contact. The secondary dressing is intended to contact intact skin only. When a dressing change is required or the wound treatment is concluded, the combination of the primary and secondary dressing has to be removed from the body of the patient in a third step of the wound treatment procedure. The dressing removal shall not be painful for the patient. In addition, the dressing removal shall not damage the skin and the wound. However, the high adhesive strength of known secondary dressings may in certain situations cause pain and skin damages when the dressing is removed from the body of the patient. This may be the case, for example, in elderly patients who in general have a more sensitive skin.

The objective of the present invention was to provide an improved medical article for fixation of a wound dressing, in particular to provide an improved medical article for fixation of a wound dressing which does not show the described drawback. Accordingly, the objective of the present invention was to provide an improved medical article for fixation of a wound dressing which may allow a more painless and more gentle dressing removal. The objective has been solved by a medical article according to claim 1 and a manufacturing method according to claim 16.

According to the invention, the medical article comprises a non-woven backing layer with a top side and a bottom side. By using a non-woven material as a backing layer the medical article may be flexible, soft, stretchable and may have pleasant haptic properties. Moreover, due to the non-woven backing the medical article may have a high moisture vapor transmission rate, that is the medical article may be highly breathable.

According to the invention, the medical article furthermore comprises a plastic film layer with a top side and a bottom side. The top side of the film layer is attached to the bottom side of the backing layer. This film layer advantageously facilitates the application of the silicone gel described in the following paragraph on the backing layer and may prevent that the silicone gel penetrates into the backing layer (barrier or seal function). Moreover, the film layer advantageously contributes to the medical article's waterproofness as well as its resistance to bacterial penetration. The film layer attached to the backing layer is designated as "first film layer" in this specification.

According to the invention, the medical article also comprises an adhesive silicone gel layer with a top side and a bottom side. The top side of the silicone gel layer is attached to the bottom side of the first film layer. Due to the silicone gel layer the medical article may be removed from the skin of the patient without causing pain or skin damages and without leaving any residue on the skin. The silicone gel layer represents an essential feature of the present invention allowing a more painless and more gentle dressing removal. At the same time, the silicone gel layer still has enough adhesive strength to securely fix the primary dressing on the body of the patient. The silicone gel may also be attached to the skin and the primary dressing multiple times, thereby allowing to reposition the medical article if required.

The medical article may optionally comprise a protection layer with a top side and a bottom side. The top side of the optional protection layer is releasably attached to the bottom side of the silicone gel layer. The protection layer prevents contamination of the silicone gel layer during storage and simplifies the application of the medical article. The protection layer is pulled off from the medical article prior its use. Since the silicone gel has a reduced adhesive strength, the removal of the protection layer from the present medical article is very easy and requires only minimal force.

In summary, the medical article according to the present invention may provide an easy to apply, secure, skin-friendly, painless and gentle fixation of a primary dressing to a body of a patient. Surprisingly, it was found that the medical article may have a comparatively high moisture vapor transmission rate. Therefore, the present medical article may be highly breathable despite comprising a plastic film layer and a silicone gel layer. The high breathability may prevent both maceration of the skin as well as a reduction of the adhesive properties of the silicone gel layer, which may result from an undesired accumulation of moisture between the skin and the silicone gel layer. Further advantages of the present medical article are described in connection with the following preferred embodiments of the invention.

Preferably, the medical article consists of the non-woven backing layer, the first plastic film layer, the adhesive silicone gel layer and optional the protection layer.

The present medical article may be cut to size. Therefore, it is possible to provide the medical article in the form of a roll. The length of the medical article may then be chosen according to the particular wound to be treated which is very convenient for the user. The medical article may also comprise separation lines that allow individual pieces to be removed from the medical article by hand without the aid of a cutting tool such as scissors. The separation lines may comprise perforations extending laterally across the medical article at regular intervals along the length of the medical article. However, it may be advantageous as well if such separation lines are not present to simplify the manufacturing process of the medical article and avoid limitations on the size of individual pieces that can be removed from the medical article. Therefore, according to a preferred embodiment of the invention the medical article does not comprise separation lines.

In a preferred embodiment of the invention the medical article including the protection layer has a thickness, determined according to EN ISO 5084, of 350 μm to 700 μm, in particular 450 μm to 600 μm. The medical article without the protection layer may have a thickness, determined according to EN ISO 5084, of 350 μm to 600 μm, in particular 450 μm to 500 μm.

In another preferred embodiment of the invention the medical article including the protection layer has a grammage, determined according to ISO 3801, of 195 $g/m^2$ to 245 $g/m^2$, in particular approximately 220 $g/m^2$. The medical article without the protection layer may have a grammage, determined according to ISO 3801, of 130 $g/m^2$ to 160 $g/m^2$, in particular approximately 145 $g/m^2$.

Preferably, the medical article has a peel adhesion at 180° on Bristol paper, determined according to FINAT No. 1, of 1.3N/25 mm to 2.1N/25 mm, in particular 1.3N/25 mm to 1.6N/25 mm. The Bristol paper may be purchased from the company Exacompta, article number 13316E. In addition, the medical article preferably has a peel adhesion between the silicone gel layer and the protection layer, determined according to ASTM D 1876, of at most 1.3N/25 mm, in particular at most 0.6N/25 mm. A medical article with peel adhesion values within these ranges may be particular advantageous regarding gentle removal of the dressing as well as easy removal of the protection layer.

The medical article may advantageously have a moisture vapor transmission rate (MVTR), determined according to EN 13726-2 (chapter 3.2), of at least 500 $g/m^2/24$ h, in particular of at least 680 $g/m^2/24$ h. In particular, the medical article has a moisture vapor transmission rate, determined according to EN 13726-2 (chapter 3.2), of at least 800 $g/m^2/24$ h. As already mentioned, a high moisture vapor transmission rate (breathability) prevents skin maceration and reduction of the adhesive strength of the medical article. However, the construction and material selection of the medical article may limit its breathability to about 1000 $g/m^2/24$ h. Therefore, the medical article may have a moisture vapor transmission rate, determined according to EN 13726-2 (chapter 3.2), of at most 1000 $g/m^2/24$ h.

The medical article may preferably have a waterproofness, determined according to EN ISO 13726-3:2002, of at most 300 s. Furthermore, the medical article may have a resistance to wet bacterial penetration, determined according to EN ISO 22610:2006, of at least 2.8, in particular at least 5. When the medical article is waterproof and resistant to bacterial penetration, contamination of the wound may be prevented. Moreover, leakage of wound exudate out of the wound dressing may then effectively be prevented.

The backing layer may comprise polyester fibers, in particular polyethylene terephthalate fibers (PET fibers). Preferably, the backing layer consists of polyester fibers, in particular polyethylene terephthalate fibers. The backing layer may preferably have a thickness of 0.37 mm to 0.54 mm, in particular approximately 0.45 mm, wherein the thickness can be determined according to EN ISO 5084. Furthermore, the backing layer may preferably have a grammage of 44 $g/m^2$ to 51 $g/m^2$, in particular approximately 47 $g/m^2$, wherein the grammage can be determined according to ISO 3801.

The first film layer may comprise polyurethane (PU). Preferably, the first film layer consists of polyurethane. The first film layer may have for example a thickness of 10 μm to 15 μm, in particular approximately 12 μm. It is also preferred that the first film layer forms a continuous layer, that is the first film layer preferably does not contain any openings, but completely covers the bottom side of the backing layer. These features, in particular the material selection regarding the first film layer, may also significantly contribute to the numerous advantages of the present medical article.

In a preferred embodiment of the invention the first film layer is a coating, in particular a transfer coating. Likewise, it is preferred that the silicone gel layer is a coating, in particular a transfer coating. Thus, the first film layer as well as the silicone gel layer are preferably generated by a coating process and in particular by a transfer coating process. Transfer coating is known in the prior art and described, for example, in U.S. Pat. No. 9,827,206 B2. The transfer coating may prevent or at least reduce an undesired penetration of the coating material into a porous substrate like the present non-woven backing layer. With regard to the present silicone gel layer, the transfer coating may allow a corona treatment of the silicone gel. This advantageously may improve the adhesion of the silicone gel on the first film layer. The coating weight of the first film layer may be 10 $g/m^2$ to 15 $g/m^2$, in particular approximately 12 $g/m^2$. A suitable and advantageous coating weight for the silicone gel layer may be a coating weight of 70 $g/m^2$ to 90 $g/m^2$, in particular approximately 80 $g/m^2$. Similar to the first film layer, the silicone gel layer preferably forms a continuous layer to achieve the desired adhesive strength.

The first film layer may be formed using a liquid coating solution of a polyurethane which may solidify upon drying. For example, the liquid coating solution may comprise a hydrophilic polyurethane and dimethyl formamide, toluene as well as isopropanol as solvents. The liquid coating solution may additionally comprise amorphous silica for mechanical reinforcement. In particular, the liquid coating solution consists of a hydrophilic polyurethane, dimethyl formamide, toluene, isopropanol and optional amorphous silica.

The adhesive silicone gel forming the adhesive silicone gel layer is a crosslinked silicone polymer with a gel-like consistency. The silicone gel is typically formed using a hydrosilation (or polyaddition) reaction between an alpha-omega vinyl terminated polydimethyl siloxane and a Si—H containing siloxane catalyzed by a platinum catalyst. Thermal curing may preferably be applied to accelerate the polymerization process. In addition, the silicone gel may be solvent free.

Adhesive silicone gels are known in the prior art, for example from US 2007/0270555 A1, and are commercially available. Generally, silicone systems to produce such silicone gels are sold by silicone manufacturers as two-component kits. The two components of the kit are mixed with each other to form the gel and may comprise:

| Part A | Part B |
|---|---|
| Mix of alpha-omega vinyl terminated polydimethyl siloxane oils<br>Pt catalyst | Mix of alpha-omega vinyl terminated polydimethyl siloxane oils<br>Mix of Si—H containing siloxane catalyzed oils<br>Pt catalyst inhibitor (i.e. ethynyl cyclohexanol and the like) |

The platinum catalyst inhibitor stabilizes the final mix, avoiding too early crosslinking of the product during coating. This volatile chemical will evaporate during curing at high temperature (100 to 180° C.). Silicone systems suitable for the present invention may be purchased from Elkem Silicones (Silbione RT Gel range or Silbione HC2 range), Wacker Silicones (Silpuran range), Dupont Liveo (soft skin adhesives MG7 range), Momentive (Silopren Gel range) and Nusil (Med Gels range). Particularly preferred is the Silbione RT Gel range from Elkem Silicones. The silicone gel of the present invention may advantageously have a gel hardness of 100 mm/10 to 220 mm/10, in particular of approximately 155 mm/10, as measured according to DIN ISO 2137 (hollow cone 62.5 g).

In the following, preferred features to facilitate the handling of the protection layer will be suggested. First of all, the protection layer may comprise a plastic film layer with a top side, a bottom side and a single wavelike cut line along its length extension. This film layer forms the main structural component of the protection layer. The film layer forming the main structural component of the protection layer is designated as "second film layer" in this specification. Due to the single cut line the second film layer consists of two parts located next to each other. The top side of the second film layer normally corresponds to the top side of the protection layer. The bottom side of the second film layer may correspond to the bottom side of the protection layer as long as no further layer is attached to the bottom side of the second film layer. The separation lines described before are different from the cut line in the protection layer and do not include the cut line in the protection layer. Therefore, a disclaimer regarding the separation lines does not rule out the presence of the cut line in the protection layer.

The second film layer and the entire protection layer, respectively, is flexible, but preferably still has a certain rigidness. The second film layer may comprise polyester, in particular polyethylene terephthalate. Preferably, the second film layer consists of polyester, in particular polyethylene terephthalate. The second film layer may advantageously have a thickness of approximately 50 μm.

In addition, the second film layer is preferably transparent and a colored tape is attached to the bottom side of the second film layer along the cut line. The cut line penetrates the second film layer and the tape. The tape may indicate the position of the cut line which might otherwise be unclear to the user due to the transparency of the second film layer. The tape usually comprises a plastic film layer as a carrier and an adhesive coating. The film layer of the tape is designated as "third film layer" in this specification. For example, the third film layer may comprise or consist of polypropylene. Similar to the second film layer, the third film layer may have a thickness of approximately 50 μm. A polymer-based dispersion may be used as adhesive coating for the tape.

It may also be advantageous if the tape is of a first color and comprises imprinted visual indicators of a second color, the second color being different from the first color. For instance, the first color may be white and the second color may be blue. Other color combinations might be chosen as well, such as white and green, white and red or white and black. Preferably, the visual indicators are formed as arrows. The arrows may indicate the direction of pull to remove the protection layer from the medical article.

The present medical article is intended for fixation of a wound dressing as already mentioned. Accordingly, subject of the present invention is also a use of a medical article according to the present invention to fix a wound dressing on a body of a patient. The wound dressing may be any wound dressing material which requires additional adhesive fixation and is suited to be used in combination with the present medical article. Typically, the wound dressing is a compress. The medical article may also be used for other purposes, for instance to fix medical cannulas or tubes on a particular site of the patient's body.

The present invention also suggests a manufacturing method for the medical article. The manufacturing method comprises the following steps:

i. Providing a non-woven backing layer with a top side and a bottom side.
ii. Coating, in particular transfer coating, of the bottom side of the backing layer with a first composition forming a first plastic film layer, said first film layer having a top side and a bottom side, wherein the top side of the first film layer is attached to the bottom side of the backing layer.
iii. Coating, in particular transfer coating, of the bottom side of the first film layer with a second composition forming an adhesive silicone gel layer, said silicone gel layer having a top side and a bottom side, wherein the top side of the silicone gel layer is attached to the bottom side of the first film layer.
iv. Optionally, providing a protection layer with a top side and a bottom side.
v. Optionally, covering the bottom side of the silicone gel layer with the protection layer, wherein the top side of the protection layer is releasably attached to the bottom side of the silicone gel layer.

The first composition as already mentioned is preferably a liquid coating solution of a polyurethane which may solidify upon removing the solvent by drying. The second composition may comprise an alpha-omega vinyl terminated polydimethyl siloxane, a Si—H containing siloxane and a platinum catalyst.

If in step ii. the transfer coating is carried out, the first composition is not directly applied to the bottom side of the backing layer. Instead, the composition is first applied to a separate substrate layer (for example an anti-adherent film), from which it is afterwards transferred to the backing layer. The transfer may be carried out by contacting the bottom side of the backing layer with the liquid composition being distributed on the substrate followed by a drying step to solidify the composition. Similarly, the second composition is not directly applied to the bottom side of the first film layer, if in step iii. the transfer coating is carried out. The composition is first applied to a separate substrate layer (for example an anti-adherent film), from which it is afterwards transferred to the first film layer. The transfer may be carried out after complete formation of the crosslinked silicone gel and preferably a corona treatment as disclosed in U.S. Pat. No. 9,827,206 B2. As substrate for the transfer coating step of the silicone gel layer the protection layer may be used.

The aforementioned use and manufacturing method of the medical article also refer to the specific embodiments previously described in connection with the medical article. That is, the further features of the previously described specific embodiments of the medical article are also part of the aforementioned use and manufacturing method.

EXAMPLE AND FIGURES

FIG. 1 shows a preferred embodiment of the medical article according to the invention. The medical article is provided in the form of a roll. The roll may comprise a strip of the medical article with a length of several meters, for example 2 meters. The depicted roll has a width of about 10 cm.

Figure 2:
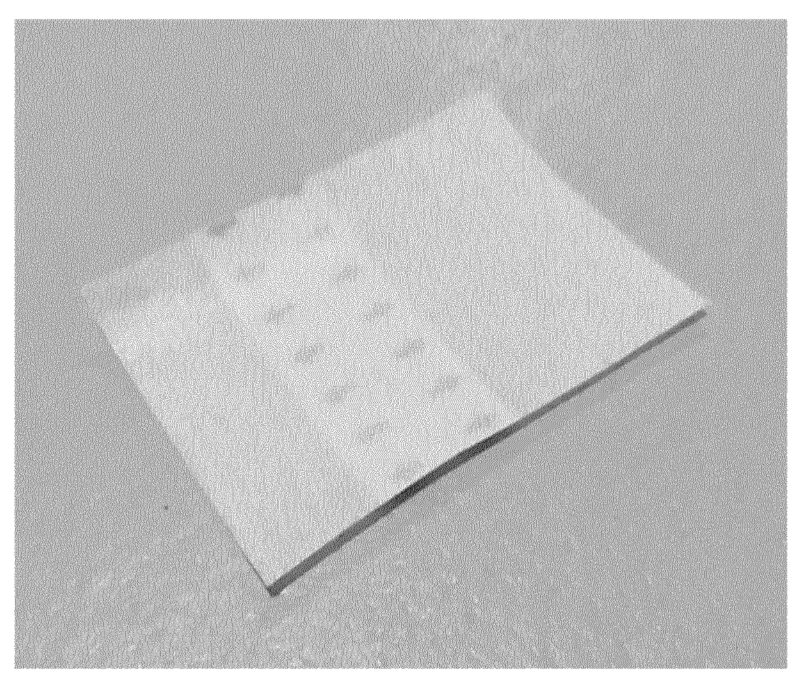

FIG. 2 shows the top side of a medical article which has been cut off from the roll of FIG. 1. The top side of the medical article is formed by a white non-woven backing layer.

Figure 3:
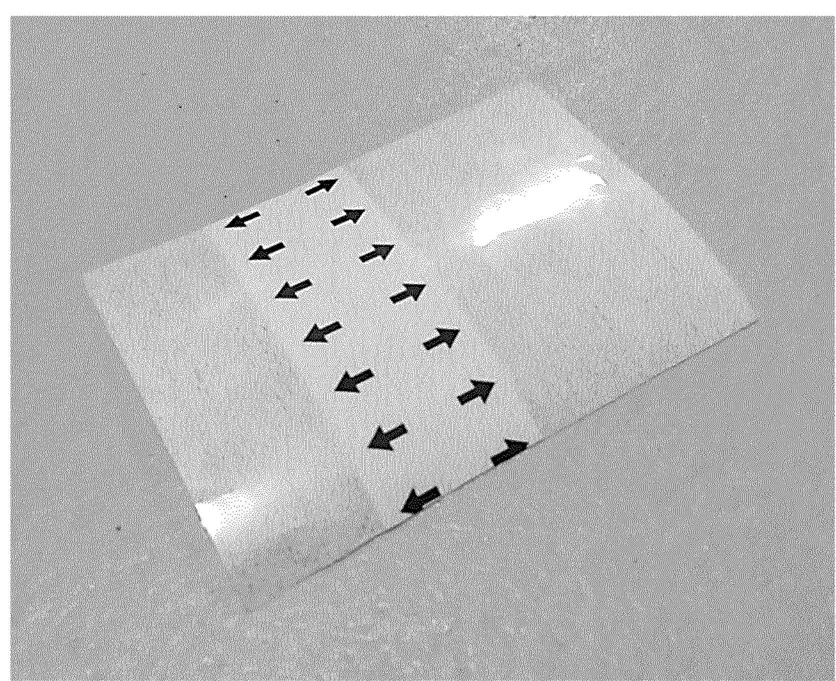
Figure 4:
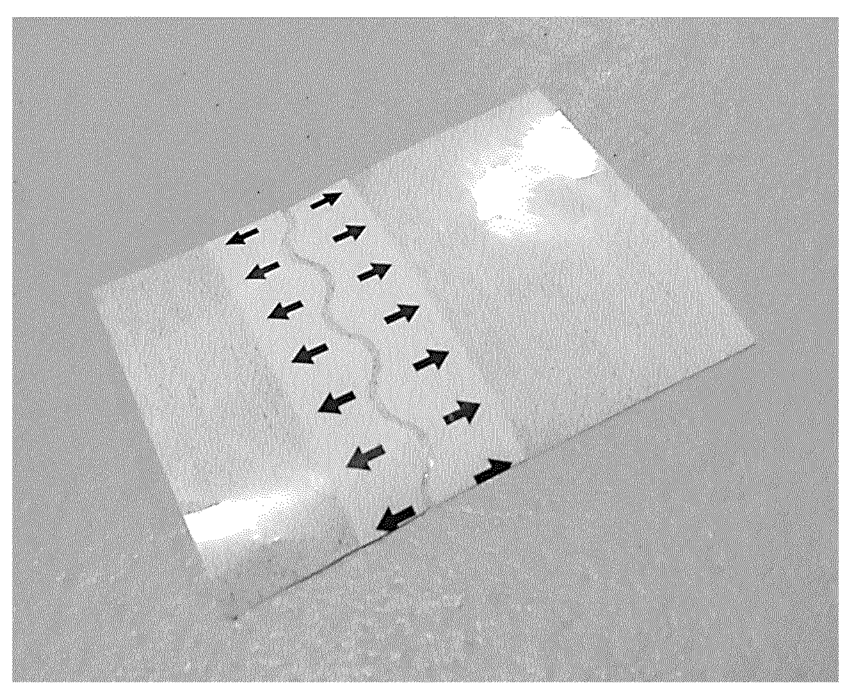

FIG. 3 shows the bottom side of the medical article of FIG. 2. The bottom side of the medical article is formed by a protection layer, which is transparent apart from a white tape with blue arrows. The tape has a width of about 3 cm. The protection layer comprises a wavelike cut line which is located approximately in the middle of the white tape between the two rows of arrows. The cut line as well as the tape with the arrows greatly facilitate the removal of the protection layer from the medical article. The cut line is hardly visible when observing a sample of the medical article. Therefore, FIG. 4 shows the medical article of FIG. 3 in a stretched configuration to better reveal the wavelike cut line of the protection layer.

Figure 5:
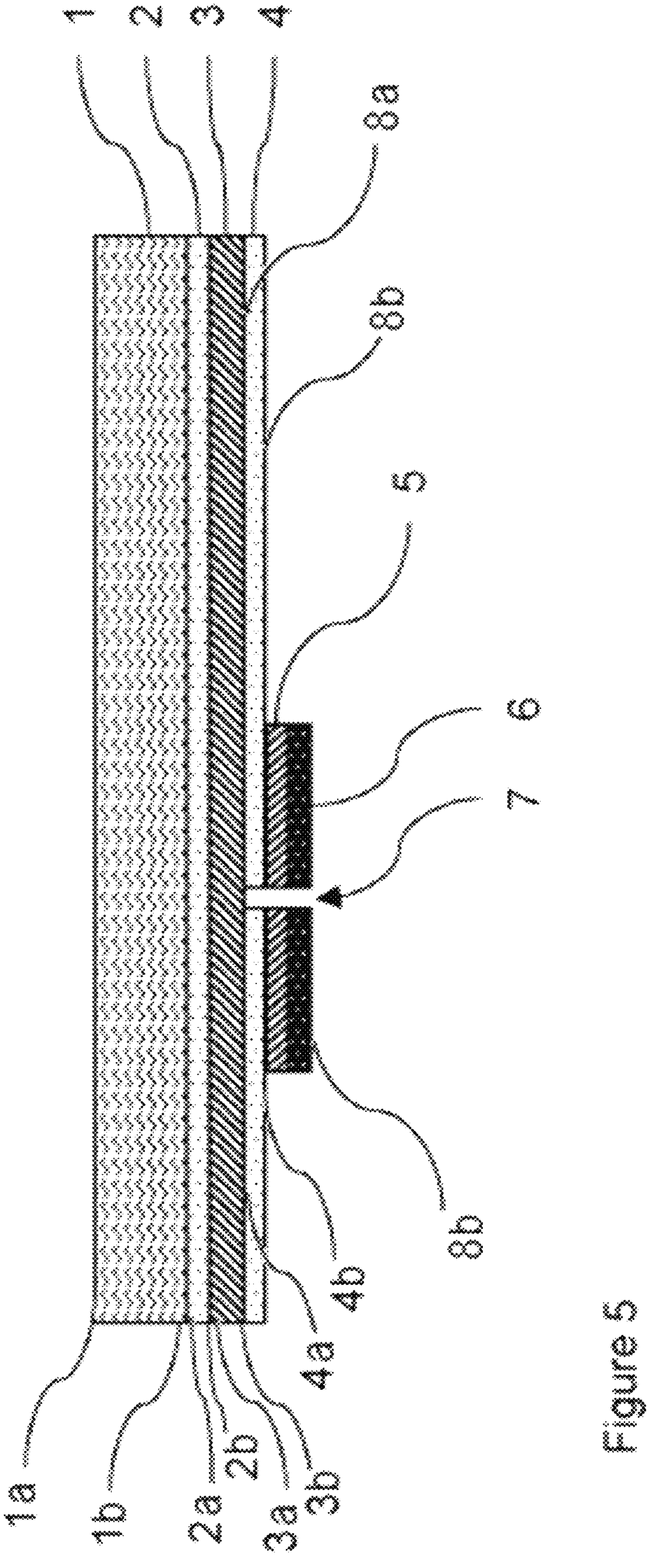

FIG. 5 finally shows a schematic cross section of the medical article depicted in the previous figures. The medical article comprises as already mentioned a white non-woven backing layer 1. The backing layer 1 may be made of polyethylene terephthalate fibers and has a top side 1*a* and bottom side 1*b*. Furthermore, the backing layer 1 may have a thickness of about 0.45 mm and a grammage of about 47 g/m$^2$. A plastic film layer 2 is attached to the bottom side 1*b* of the backing layer 1, which is preferably formed as a coating. The film layer 2 may be made of polyurethane and has a top side 2*a* and bottom side 2*b*. Moreover, the film layer 2 may have a thickness of about 12 μm and a coating weight of about 12 g/m$^2$. An adhesive silicone gel layer 3 is then attached to the bottom side 2*b* of the film layer 2, which is preferably formed as a coating as well. The coating weight of the silicone gel layer 3 may amount to about 80 g/m$^2$. The silicone gel layer 3 has a top side 3*a* and bottom side 3*b* and is covered until use of the medical article by a protection layer (combination of 4, 5, 6) already known from the previous figures. The protection layer comprises as main structural component a transparent second plastic film layer 4 and a white tape 5, 6 with blue arrows (the arrows are not shown in FIG. 5). The arrow tape of the protection layer is a striking optical feature of the medical article as can be easily seen in the previous figures. Film layer 4 may be made of polyethylene terephthalate has a top side 4*a* and bottom side 4*b*. Reference sign 5 indicates an adhesive coating, for example a polymer-based dispersion, of the tape to attach it on the film layer 4, wherein reference sign 6 indicates a further plastic film layer forming the carrier of the tape. Film layer 6 of the tape may be made of polypropylene. Film layers 4 and 6 may both have a thickness of about 50 μm and a surface weight of about 70 g/m$^2$. Finally, a wave-shaped cut line 7 is present in the protection layer as mentioned before. The cut line 7 divides the protection layer 4, 5, 6 in two parts. To remove the protection layer, the user may bend the medical article along the white tape. This opens the cut line 7 and detaches the two parts of the protection layer from the silicone gel layer 3 in the bended region. The user may then grip each part of the protection layer and pull it off in the direction indicated by the arrows. The top side 4*a* of the second film layer 4 normally corresponds to the top side 8*a* of the protection layer. The bottom side 4*b* of the second film layer 4 may correspond to the bottom side 8*b* of the protection layer as long as no further layer is attached to the bottom side 4*b* of the second film layer 4.

The following table summarizes further features, which the medical article according to the described example may possess. The values mentioned in the table are average values.

| Feature of the medical article | Test method | Value (average) |
|---|---|---|
| Grammage without protection layer | ISO 3801 | 145 g/m$^2$ |
| Peel adhesion at 180° on bristol paper | FINAT No. 1 | 1.5N/25 mm |
| Peel adhesion between silicone gel and protection layer | ASTM D 1876 | 0.04N/25 mm |
| Moisture vapor transmission rate (MVTR) | EN 13726-2 (chapter 3.2) | 830 g/m$^2$/24 h |
| Waterproofness | EN ISO 13726-3: 2002 | >300 s |
| Resistance to wet bacterial penetration | EN ISO 22610: 2006 | 5.93 |

The invention claimed is:

1. A medical article for fixation of a wound dressing, consisting of: a non-woven backing layer (1) with a top side (1*a*) and a bottom side (1*b*), a first plastic film layer (2) with a top side (2*a*) and a bottom side (2*b*), wherein the top side of the first plastic film layer (2*a*) is attached to the bottom side of the non-woven backing layer (1*b*), an adhesive silicone gel layer (3) with a top side (3*a*) and a bottom side (3*b*), wherein the top side of the adhesive silicone gel layer (3*a*) is attached to the bottom side of the first plastic film layer (2*b*), and a protection layer (4, 5, 6) with a top side (8*a*) and a bottom side (8*b*), wherein the top side of the protection layer (8*a*) is releasably attached to the bottom side of the adhesive silicone gel layer (3*b*), wherein the protection layer (4, 5, 6) comprises a second plastic film layer (4) with a top side (4*a*), a bottom side (4*b*) and a single wave-shaped cut line (7) along its length extension, and wherein the second plastic film layer (4) is transparent, and a colored tape (5, 6) is attached to the bottom side of the second plastic film layer (4*b*) along the single wave-shaped cut line (7), wherein the single wave-shaped cut line (7) also penetrates the colored tape (5, 6).

2. A medical article according to claim 1, wherein the medical article has a peel adhesion at 180° on Bristol paper, determined according to FINAT No. 1, from 1.3 N/25 mm to 2.1 N/25 mm.

3. A medical article according to claim 2, wherein the medical article has a peel adhesion at 1800 on Bristol paper, determined according to FINAT No. 1, from 1.3 N/25 mm to 1.6 N/25 mm.

4. A medical article according to claim 1, wherein the medical article has a moisture vapor transmission rate, determined according to EN 13726-2 (chapter 3.2), of at least 500 g/m$^2$/24 h.

5. The medical article according to claim 4, wherein the medical article has a moisture vapor transmission rate, determined according to EN 13726-2 (chapter 3.2), of at least 680 g/m$^2$/24 h.

6. A medical article according to claim 1, wherein the medical article has a resistance to wet bacterial penetration, determined according to EN ISO 22610:2006, of at least 2.8.

7. The medical article according to claim 6, wherein the medical article has a resistance to wet bacterial penetration, determined according to EN ISO 22610:2006, of at least 5.

8. A medical article according to claim 1, wherein the first plastic film layer (2) is a coating.

9. A medical article according to claim 8, wherein the coating is a transfer coating.

10. A medical article according to claim 1, wherein the adhesive silicone gel layer (3) is a coating.

11. A medical article according to claim 10, wherein the coating is a transfer coating.

12. A method of manufacturing a medical article according to claim 1, comprising the steps of: i. providing a non-woven backing layer (1) with a top side (1*a*) and a bottom side (1*b*), ii. coating the bottom side of the backing layer (1*b*) with a first composition forming a first plastic film layer (2), said first plastic film layer (2) having a top side (2*a*) and a bottom side (2*b*), wherein the top side of the first plastic film layer (2*a*) is attached to the bottom side of the backing layer (1*b*), iii. coating of the bottom side of the first plastic film layer (2*b*) with a second composition forming an adhesive silicone gel layer (3), said adhesive silicone gel layer (3) having a top side (3*a*) and a bottom side (3*b*), wherein the top side of the adhesive silicone gel layer (3*a*) is attached to the bottom side of the first plastic film layer (2*b*), and iv. providing a protection layer (4, 5, 6) with a top side (8*a*) and a bottom side (8*b*), and v. covering the bottom side of the silicone gel layer (3*b*) with the protection layer (4, 5, 6), wherein the top side of the protection layer (8*a*) is releasably attached to the bottom side of the silicone gel layer (3*b*).

13. The method according to claim 12, wherein the coating step is a transfer coating step.

14. A medical article according to claim 1, wherein the medical article is provided in the form of a roll.

15. A medical article according to claim 1, wherein the medical article does not comprise separation lines.

16. A medical article according to claim 1, wherein the medical article has a waterproofness, determined according to EN ISO 13726-3:2002, of at most 300 s.

17. A medical article according to claim 1, wherein the first plastic film layer (2) comprises polyurethane.

18. A medical article according to claim 1, wherein the first plastic film layer (2) has a coating weight from 10 $g/m^2$ to 15 $g/m^2$.

19. A medical article according to claim 1, wherein the adhesive silicone gel layer (3) has a coating weight from 70 $g/m^2$ to 90 $g/m^2$.

20. A medical article according to claim 1, wherein the first plastic film layer (2) is formed using a liquid coating solution of a polyurethane.

21. A method of fixing a wound dressing comprising applying the medical article of claim 1 on a body of a patient in need of a wound dressing.

22. A medical article according to claim 1, wherein the first plastic film layer (2) consists of polyurethane.

* * * * *